United States Patent
Jayaraman

(10) Patent No.: US 7,000,305 B2
(45) Date of Patent: Feb. 21, 2006

(54) METHOD FOR MANUFACTURING A WIRE STENT COATED WITH A BIOCOMPATIBLE FLUOROPOLYMER

(75) Inventor: Swaminathan Jayaraman, Fremont, CA (US)

(73) Assignee: Vascular Concepts Holding Limited, (VG)

( * ) Notice: Subject to any disclaimer, the term of this patent is extended or adjusted under 35 U.S.C. 154(b) by 225 days.

(21) Appl. No.: 10/720,552

(22) Filed: Nov. 24, 2003

(65) Prior Publication Data

US 2004/0133272 A1    Jul. 8, 2004

Related U.S. Application Data

(63) Continuation of application No. 09/672,422, filed on Sep. 28, 2000, now Pat. No. 6,652,574.

(51) Int. Cl.
*A61F 2/02*   (2006.01)

(52) U.S. Cl. ............ 29/458; 29/527.1; 29/527.2; 427/2.1; 427/2.24; 623/1.46; 623/1.5; 623/1.53

(58) Field of Classification Search ........... 29/447, 29/458, 527.1, 527.2; 427/2.1, 2.24; 623/1.13, 623/1.18, 1.2, 1.22, 1.33, 1.46, 1.5, 1.53
See application file for complete search history.

(56) References Cited

U.S. PATENT DOCUMENTS

| | | |
|---|---|---|
| 2,524,661 A | 10/1950 | Harder et al. |
| 3,466,166 A | 9/1969 | Levinstein et al. |
| 3,562,024 A | 2/1971 | Smith |
| 3,657,744 A | 4/1972 | Ersek |
| 4,023,557 A | 5/1977 | Thorne et al. |
| 4,281,419 A | 8/1981 | Treace |
| 4,300,244 A | 11/1981 | Bokros |
| 4,409,172 A | 10/1983 | Ward, Jr. et al. |
| 4,441,215 A | 4/1984 | Kaster |
| 4,465,481 A | 8/1984 | Blake |
| 4,573,242 A | 3/1986 | Lankton et al. |
| 4,600,446 A | 7/1986 | Torisaka et al. |
| 4,640,320 A | 2/1987 | Avison et al. |
| 4,655,771 A | 4/1987 | Wallsten |
| 4,669,474 A | 6/1987 | Barrows |
| 4,718,907 A | 1/1988 | Karwoski et al. |
| 4,719,916 A | 1/1988 | Ravo |
| 4,732,152 A | 3/1988 | Wallsten et al. |
| 4,733,665 A | 3/1988 | Palmaz |
| 4,752,054 A | 6/1988 | Jonsson |
| 4,762,128 A | 8/1988 | Rosenbluth |
| 4,776,337 A | 10/1988 | Palmaz |
| 4,813,416 A | 3/1989 | Pollak et al. |
| 4,816,339 A | 3/1989 | Tu et al. |
| 4,866,816 A | 9/1989 | Caveney |
| 4,877,030 A | 10/1989 | Beck et al. |
| 4,878,906 A | 11/1989 | Lindemann et al. |

(Continued)

FOREIGN PATENT DOCUMENTS

WO    WO 96/00103 A1    1/1996

(Continued)

*Primary Examiner*—David P. Bryant
*Assistant Examiner*—Jermie E. Cozart
(74) *Attorney, Agent, or Firm*—Fleit Kain Gibbons Gutman Bongini & Bianco; Paul D. Bianco; Martin Fleit

(57) ABSTRACT

A method for manufacturing a stent includes heating a plurality of wire strands to impart a desired shape to the wire strands, coating each wire strand with a biocompatible polymer in an extruder to produce a plurality of coated wire strands, and interlacing the coated wire strands to form a stent.

20 Claims, 4 Drawing Sheets

U.S. PATENT DOCUMENTS

| | | |
|---|---|---|
| 4,879,135 A | 11/1989 | Greco et al. |
| 4,902,290 A | 2/1990 | Fleckenstein et al. |
| 4,950,285 A | 8/1990 | Wilk |
| 4,986,831 A | 1/1991 | King et al. |
| 4,990,158 A | 2/1991 | Kaplan et al. |
| 5,007,926 A | 4/1991 | Derbyshire |
| 5,059,166 A | 10/1991 | Fischell et al. |
| 5,059,211 A | 10/1991 | Stack et al. |
| 5,061,276 A * | 10/1991 | Tu et al. .................... 623/1.33 |
| 5,064,435 A | 11/1991 | Porter |
| 5,078,726 A | 1/1992 | Kreamer |
| 5,078,736 A | 1/1992 | Behl |
| 5,084,065 A | 1/1992 | Weldon et al. |
| 5,100,429 A | 3/1992 | Sinofsky et al. |
| 5,104,403 A | 4/1992 | Brotzu et al. |
| 5,107,852 A | 4/1992 | Davidson et al. |
| 5,116,360 A | 5/1992 | Pinchuk et al. |
| 5,123,917 A | 6/1992 | Lee |
| 5,147,385 A | 9/1992 | Beck et al. |
| 5,156,620 A | 10/1992 | Pigott |
| 5,156,623 A | 10/1992 | Hakamatsuka et al. |
| 5,158,548 A | 10/1992 | Lau et al. |
| 5,163,951 A | 11/1992 | Pinchuk et al. |
| 5,180,366 A | 1/1993 | Woods |
| 5,192,307 A | 3/1993 | Wall |
| 5,192,310 A | 3/1993 | Herweck et al. |
| 5,192,311 A | 3/1993 | King et al. |
| 5,195,984 A | 3/1993 | Schatz |
| 5,197,977 A | 3/1993 | Hoffman, Jr. et al. |
| 5,217,026 A | 6/1993 | Stoy et al. |
| 5,234,456 A | 8/1993 | Silvestrini |
| 5,234,457 A | 8/1993 | Andersen |
| 5,258,020 A | 11/1993 | Froix |
| 5,279,594 A | 1/1994 | Jackson |
| 5,282,823 A | 2/1994 | Schwartz et al. |
| 5,282,824 A | 2/1994 | Gianturco |
| 5,289,831 A | 3/1994 | Bosley |
| 5,290,271 A | 3/1994 | Jernberg |
| 5,304,220 A | 4/1994 | Maginot |
| 5,306,286 A | 4/1994 | Stack et al. |
| 5,330,500 A | 7/1994 | Song |
| 5,366,504 A | 11/1994 | Andersen et al. |
| 5,383,926 A | 1/1995 | Lock et al. |
| 5,387,235 A | 2/1995 | Chuter |
| 5,389,106 A | 2/1995 | Tower |
| 5,456,713 A | 10/1995 | Chuter |
| 5,507,771 A | 4/1996 | Gianturco |
| 5,522,881 A | 6/1996 | Lentz |
| 5,556,414 A | 9/1996 | Turi |
| 5,607,478 A | 3/1997 | Lentz et al. |
| 5,628,787 A | 5/1997 | Mayer |
| 5,630,840 A | 5/1997 | Mayer |
| 5,632,840 A | 5/1997 | Campbell |
| 5,649,977 A | 7/1997 | Campbell |
| 5,674,241 A | 10/1997 | Bley et al. |
| 5,674,276 A * | 10/1997 | Andersen et al. ............ 623/1.5 |
| 5,679,470 A | 10/1997 | Mayer |
| 5,700,285 A | 12/1997 | Myers et al. |
| 5,700,286 A | 12/1997 | Tartaglia et al. |
| 5,718,159 A | 2/1998 | Thompson |
| 5,725,570 A | 3/1998 | Heath |
| 5,741,325 A | 4/1998 | Chaikof et al. |
| 5,766,204 A | 6/1998 | Porter et al. |
| 5,770,819 A | 6/1998 | Mehan |
| 5,800,511 A | 9/1998 | Mayer |
| 5,824,046 A | 10/1998 | Smith et al. |
| 5,824,077 A | 10/1998 | Mayer |
| 5,836,925 A | 11/1998 | Soltesz |
| 5,836,962 A | 11/1998 | Gianotti |
| 5,843,158 A | 12/1998 | Lenker et al. |
| 5,843,166 A | 12/1998 | Lentz et al. |
| 5,849,037 A * | 12/1998 | Frid .......................... 623/1.2 |
| 5,855,600 A | 1/1999 | Alt |
| 5,858,556 A | 1/1999 | Eckert et al. |
| 5,910,168 A | 6/1999 | Myers et al. |
| 5,913,896 A | 6/1999 | Boyle et al. |
| 5,927,345 A | 7/1999 | Samson |
| 5,957,954 A | 9/1999 | Badalamenti et al. |
| 5,961,545 A | 10/1999 | Lentz et al. |
| 5,980,531 A | 11/1999 | Goodin et al. |
| 5,980,564 A | 11/1999 | Stinson |
| 6,015,432 A | 1/2000 | Rakos et al. |
| 6,027,779 A | 2/2000 | Campbell et al. |
| 6,053,943 A * | 4/2000 | Edwin et al. .............. 623/1.25 |
| 6,077,296 A | 6/2000 | Shokoohi et al. |
| 6,090,134 A | 7/2000 | Tu et al. |
| 6,161,399 A * | 12/2000 | Jayaraman ................... 66/170 |
| 6,162,537 A | 12/2000 | Martin et al. |
| 6,165,211 A * | 12/2000 | Thompson ................ 623/1.13 |
| 6,187,039 B1 | 2/2001 | Hiles et al. |
| 6,214,040 B1 | 4/2001 | Jayaraman |
| 6,342,068 B1 | 1/2002 | Thompson |
| 6,357,104 B1 * | 3/2002 | Myers ...................... 29/527.1 |
| 6,364,903 B1 | 4/2002 | Tseng et al. |
| 6,364,904 B1 | 4/2002 | Smith |
| 6,475,235 B1 * | 11/2002 | Jayaraman ................ 623/1.15 |
| 6,547,814 B1 | 4/2003 | Edwin et al. |
| 6,592,617 B1 * | 7/2003 | Thompson ................ 623/1.53 |
| 2002/0065545 A1 | 5/2002 | Leonhardt et al. |
| 2002/0161392 A1 | 10/2002 | Dubrul |

FOREIGN PATENT DOCUMENTS

| | | |
|---|---|---|
| WO | WO 97/40755 A1 | 11/1997 |
| WO | WO 99/32051 A1 | 7/1999 |

* cited by examiner

METHOD FOR MANUFACTURING A WIRE STENT COATED WITH A BIOCOMPATIBLE FLUOROPOLYMER

CROSS-REFERENCE TO RELATED APPLICATION

This application is a continuation of U.S. application Ser. No. 09/672,422, filed Sep. 28, 2000 now U.S. Pat. No. 6,652,574. Benefit of the earlier filing date is claimed in accordance with 35 U.S.C. §120.

BACKGROUND OF THE INVENTION

The present invention relates to wire stents and related vascular devices. More particularly, it refers to a stent or other vascular positioned device containing a wire coated with a biocompatible fluoropolymer.

My prior application includes stents made from interwoven groups of yarn filaments containing a wire. U.S. Pat. No. 6,161,399 issued Dec. 19, 2000 and entitled, "Process for Manufacturing a Wire Reinforced Monolayer Fabric Stent" is hereby incorporated by reference. In addition, U.S. Pat. No. 5,961,545 describes wire stents immobilized longitudinally between tubes of expandable polytetrafluoroethylene. U.S. Pat. No. 5,957,954 describes braiding a stent and a polytetrafluoroethylene textile strand sleeve together in an axial alignment. U.S. Pat. No. 6,015,432 describes an endovascular tube made from woven graft material with a wire employed in openings in the weave. U.S. Pat. No. 5,741,325 describes a self-expanding intraluminal prosthesis containing interwoven fibers including reinforcing wire. U.S. Pat. No. 5,607,478 describes how to make a prosthesis from an expanded polytetrafluoroethylene (ePTFE) tube with a winding of PTFE.

It also is well known in the prior art to coat insulated wire with foamed fluoropolymer insulation as described in U.S. Pat. No. 5,770,819. None of these prior art disclosures teach how to coat a wire used in a prosthesis with a porous expanded PTFE to create uniform expansion of the prosthesis.

SUMMARY OF THE INVENTION

I have now invented a process to improve my stent of U.S. Pat. No. 6,161,399 by coating the plurality of wire strands of the stent with a porous expanded PTFE. The addition of expanded PTFE to the wire strand reduces platelet adhesion to the stent product. Restenosis will not occur since tissue and cells will not adhere to the expanded PTFE.

The process of this invention is achieved by pretreating a spool of wire to achieve a predetermined shape to the wire and returning the treated wire to its spool. The wire is then fed into an ePTFE extrusion machine where the wire feed is regulated depending on the speed of the extrusion machine. The wire is fed first into a nozzle of the extruder, the nozzle having a concentric opening in which the ePTFE is heated, sintered and then extruded. A laser determines the thickness of the ePTFE layer to maintain uniformity on the wire. The ePTFE coated wire is then respooled and interlaced by braiding or knitting with other coated wire. Various angles are formed with the coated wire which determines the radial and axial compressibility of the resulting stent.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
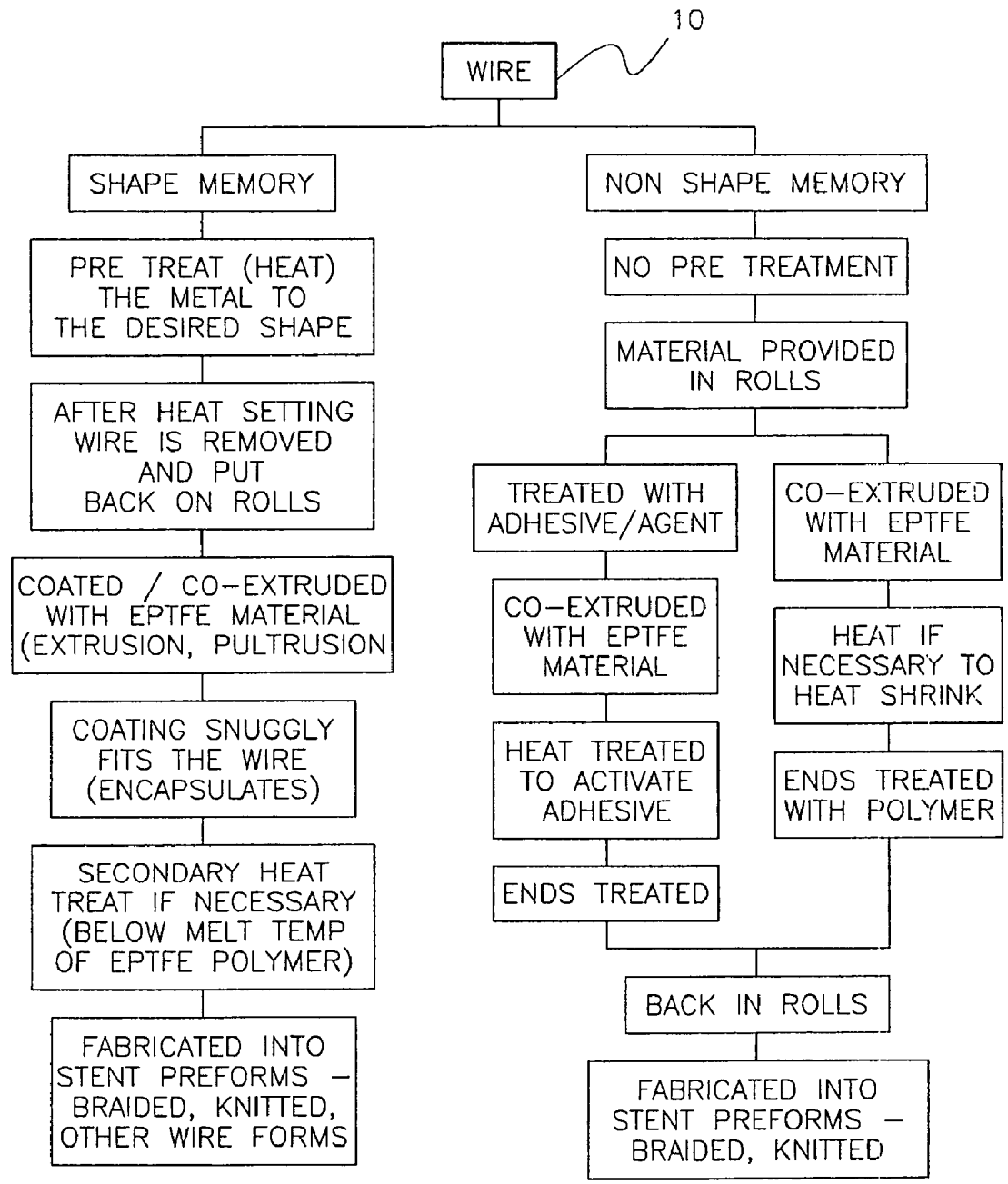
FIG. 1 is a flow diagram showing the process of this invention.

Throughout the following detailed description, the same reference numerals refer to the same element in all figures.

Figure 2:
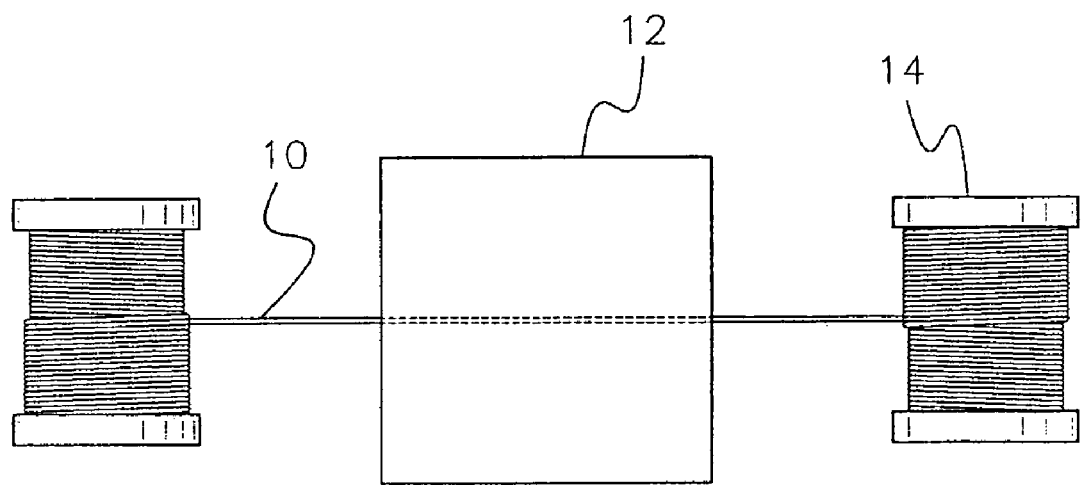
FIG. 2 shows the wire preheated.

Referring to FIG. 1, an expandable wire 10 suitable for use in a stent is chemically treated to remove surface oxidation and is then shaped and preheated in an oven 12 as shown in FIG. 2 to impart a desired shape to the wire. Alternatively, a plurality of wire strands are introduced in the oven simultaneously, heat set, then removed and put back on individual spools. These spools are sent to the coating step shown in FIG. 3. Alternatively, as shown in FIG. 1, the fluoropolymer can be adhesively applied to the wire 10.

Typical wire 10 for use in this invention is nickel-titanium alloy known as NITINOL™, stainless steel, titanium, tungsten, platinum, gold, silver or other like malleable metal that will retain a memory after heat treatment.

Figure 3:
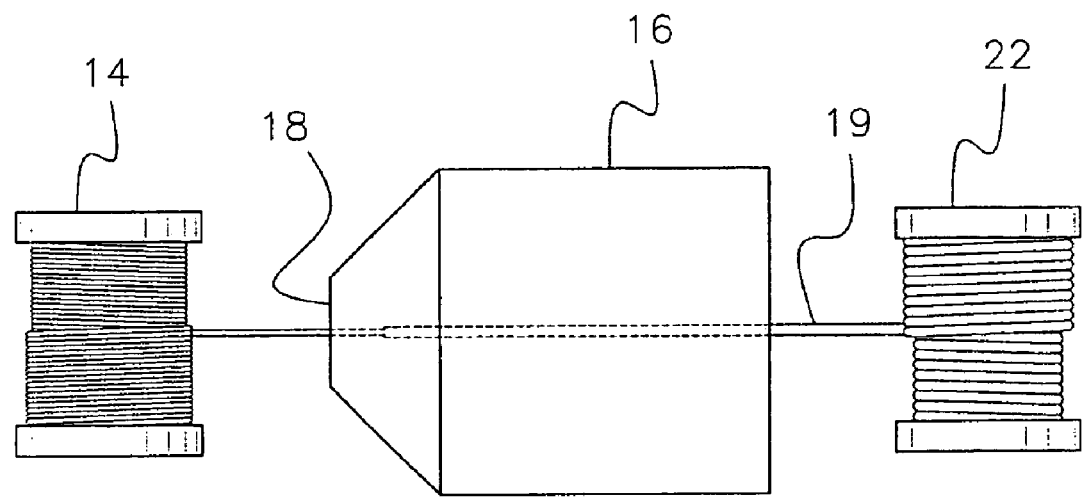
FIG. 3 shows the application of the fluoropolymer to the wire.
Figure 4:
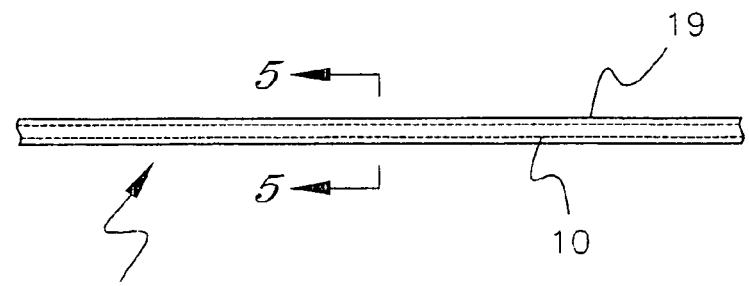
FIG. 4 is a longitudinal section of the fluoropolymer coated wire.
Figure 5:
FIG. 5 is a cross-section of the coated wire of FIG. 4 along line 5—5.

After heat treating NITINOL™ between 500–600 degrees C. for two to ten minutes, the NITINOL™ wire 10 is respooled 14 as shown in FIG. 2 and is then passed through an extruder 16 as shown in FIG. 3. Individual wire which is not heat set is braided into the desired shape and then heat set at the above temperature for substantially the same time period. The wire is then removed from the braid and heat set again. After coating, the wire is rebraided back to its original shape. The extruder 16 contains porous expanded PTFE at about 250 degrees F., which is applied to the wire to a thickness of 1–8 μm as shown in FIGS. 3 to 5. The extruder 16 has a conical opening 18 through which the wire 10 passes. The speed of the wire is regulated depending on the speed of the extrusion process to provide a uniform coating of the fluoropolymer 19 on the wire 10. The ePTFE coating 19 fits snugly around the wire with no wire surface exposed. The ePTFE has a porous structure as described in U.S. Pat. No. 5,607,478, hereby incorporated by reference. The porosity of the ePTFE surface is between 10 to 260 microns. The porosity can vary between the outer and inner surface with the outer surface having a larger porosity. It is preferred to have the same porosity throughout the coating.

Figure 6:
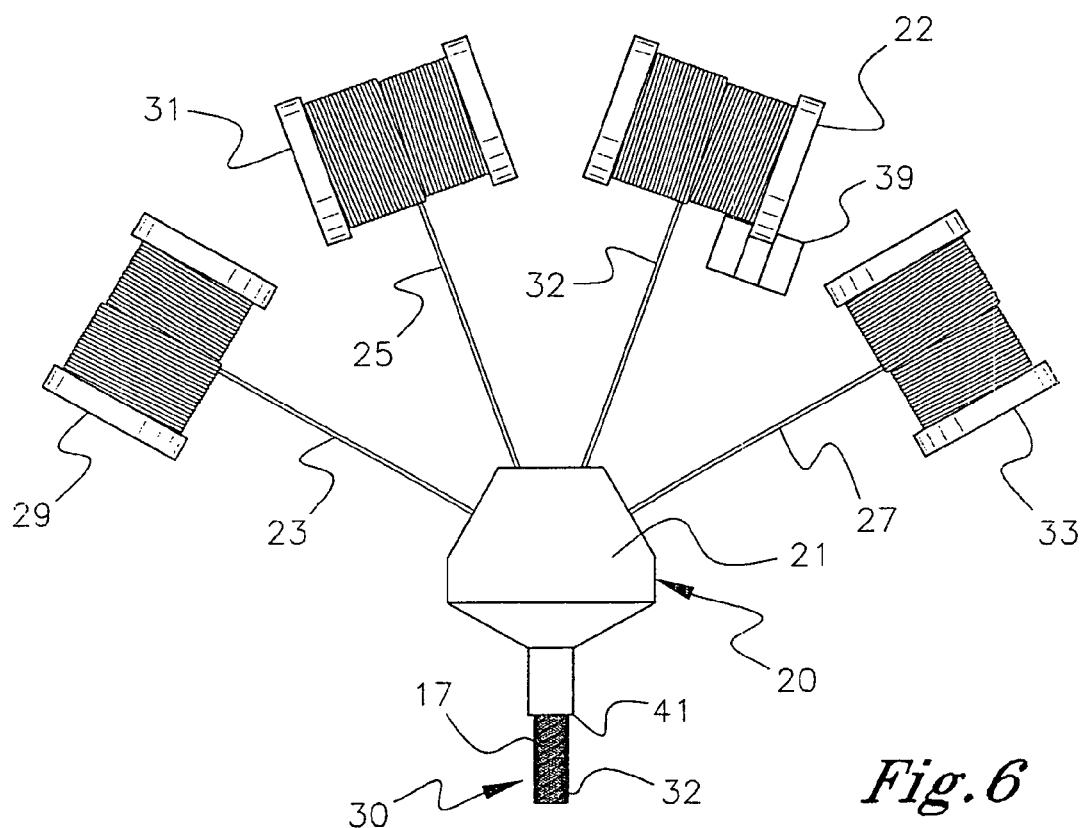
FIG. 6 shows the interlacing of the coated wire in a braiding machine to produce a tubular stent.
Figures 7, 8:
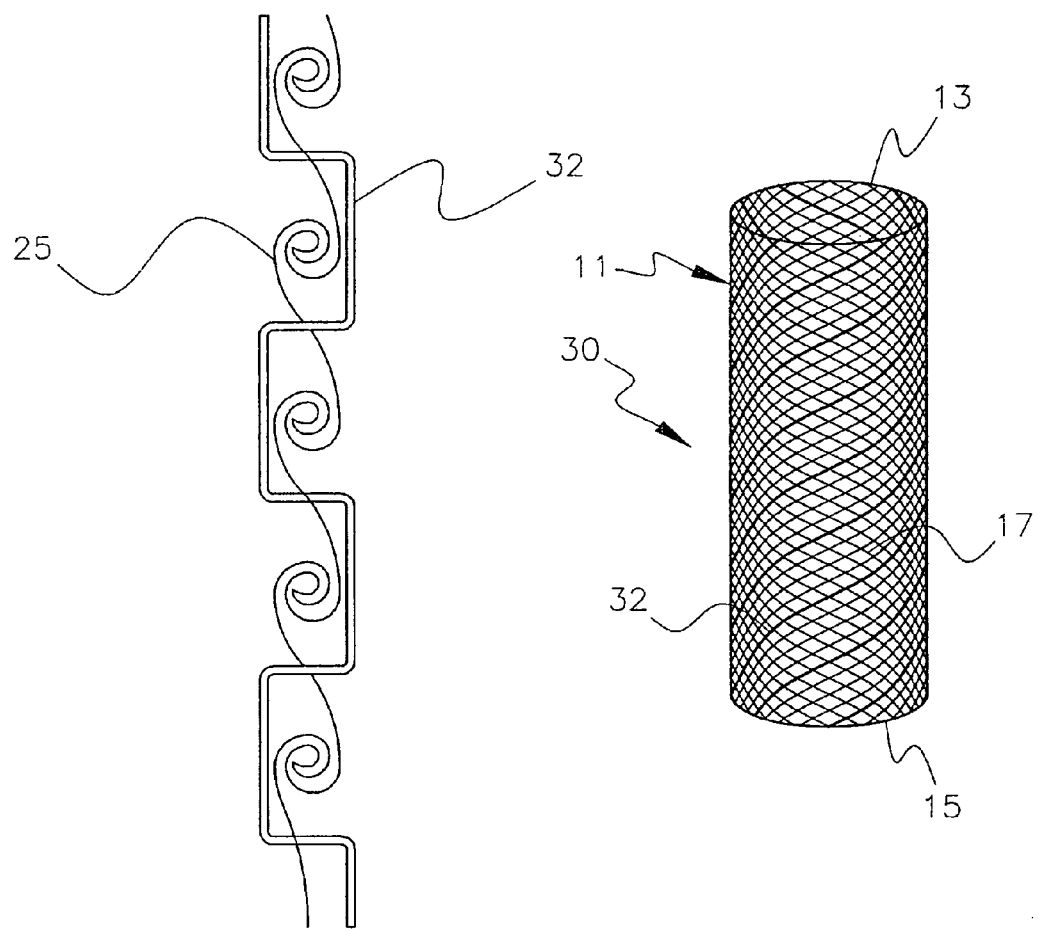
FIG. 7 is a side view of a coiled coated wire strand interlaced into the tubular stent.
FIG. 8 is a front view of a stent prepared by the process of this invention.

The wire containing the fluoropolymer coating is then respooled 22 and used in the knitting or braiding machine 20 shown in FIG. 6 to produce a stent 30 as shown in FIG. 8. The stent 30 has a tubular body 11 having a generally circular open ends 13 and 15. Body 11 consists of interlaced wire strands, each wire strand coated with ePTFE. Other biocompatible fluoropolymers such as PTFE and FEP can be substituted for the ePTFE. However, ePTFE is preferred for the wire coating.

The stent 30 is formed by two dimensional braiding in which the coated wire strands are crossed on top of each other so that strands in the final stent product are tightly held together. Depending on the type of crossing pattern employed and number of coated wire strands fed into the braid, the resulting braid will vary in its properties, i.e., axial and radial strength and compressibility. In contrast, three dimensional braiding as used in some prior art stents constitute materials superimposed concentrically over each other. This latter type of stent has a substantially thicker wall than the present invention of a braided two dimensional stent.

Although the preferred stent of the present invention employs about twenty-four interlaced coated wires represented by wire strands 23, 25, 27 and 32 in FIG. 6, stent 30 is not limited thereto and can be configured with multiple coated wires of more or less than twenty-four strands. Thirty-six or more coated wire strands would be acceptable.

Stent 30 of the present invention is made using a braiding or knitting machine 20 schematically depicted in FIG. 6. FIG. 6 is illustrative of the inventive knitting machine used to create one of the stents of the present invention. The preferred stent, as in FIG. 8, would be made from knitting machine 20 employing about four coated wire strands.

As seen in FIG. 6, knitting machine 20 includes an intake section 21 receiving strands 23, 25, 32 and 27 of coated wire from three spools of wire 29, 31, 22 and 33, respectively. Spool of wire 22 has a braking mechanism 39. An out take 41 of the knitting machine 20 is seen to have, emanating therefrom, the knitted stent 30 having the coated wire 23, 25, 32 and 27 spiraling therethrough.

In the preferred method of knitting the stent 30, the spool 22 is caused to supply coated wire 32 at a slower supply rate than is the case for the coated wire strands 23, 25 and 27. For this purpose, the brake mechanism 39 is activated to a desired degree of braking force to slow down the supply of coated wire 32 to a ratio of, for example, 1:4 as compared to the speed of supply of the strands 23, 25 and 27 of coated wire.

As a result of this knitting technique, a stent 30 is woven having a coated wire strand 32 braided about the other wire strands, locking the wire together and thereby providing a stent with increased axial and radial strength and resistance to restenosis and platelet adhesion to the stent 30.

In the braiding of the coated wire strands, the wire strands are crossed on top of each other so that the coating is tightly held because of the crossing pattern to produce a stent with low porosity. The crossing pattern determines the appearance of the surface, radial strength of the stent graft and the compressibility in both the radial and axial direction. Compressibility in the longitudinal or axial direction provides a low profile for the stent as it is introduced into a body lumen.

The coated wire strands determine the wall thickness for a particular diameter of the stent. For example, in a 4 mm coated wire the feed ratio of strands to be braided are different from the feed ratios that are required for a 6 mm stent graft. The preferred number of wire strands insures a small enough stent so it can be moved through the smallest possible hole. Variations in the coated metal strand thickness or shape also alters the thickness of the stent wall diameter.

This invention produces a stent that may or may not have areas of blood leakage, but does provide for passage of ions necessary for proper lumen wall function. The surface coverage is necessary to control areas of higher leakage of blood. The stent should have a uniform micro porous wall which determines the success of an implant. Blood needs to sweat through the holes, but not leak through the walls.

Compliance of the stent is a factor directly related to the porosity. The more porous the stent graft, the more compliant it is. An optimal compliance is sought which is essential to impart the pulsable nature of the natural arterial wall into the prosthesis.

The coated wire strands can be introduced into the braid in separate spools or they can be mixed together in one spool and then introduced into the process. Alternatively, the coated wire strands could be braided into a two strand mixture and then fed by several spools to form a braid. A wire strand 25 can be coiled as seen in FIG. 7.

The stent 30 also could have fabric incorporated between the coated wire braided structure. The wall thickness of the stent is such that in the compressed state, a double wall thickness is at least one-fifth an end diameter of the stent. For example, if the final end diameter of the stent is 6 mm, the compressed double wall thickness is less than 1.20 mm.

If fabric material is employed, such fabric material can be, for example, polyester, polypropylene, polyethylene, polyurethane, polytetrafluoroethylene or other natural fabric materials. Such strands of yarn can be monofilament or multi-filament. If monofilament strands are used, the strands can be twisted or wound prior to being fed into the knitting machine 20. The coated wire strands can have a diameter of approximately 0.004 inches and will have a greater thickness than that of the yarn.

As shown in FIG. 1 on the right side, an alternative process involves no pretreatment of the wire and the ePTFE is co-extruded with the wire and an adhesive agent. The co-extruded wire/ePTFE is then heat treated to activate the adhesive and the ends are treated before placing back on the rolls for use in the braiding or knitting machine to make a stent.

The ends of the coated wire can be terminated using a biocompatible glue (the coating is glued to the wire), ultrasonically welded, or the wire can be looped around and welded such that there is a small loop at the ends. This prevents the fraying of the wire and also prevents the coating from fraying. When the ends are looped around and welded, there are no sharp ends of the metal and this prevents any injury or trauma to the vessel wall.

The braided or knitted stent fabricated from coated wires as described above has radial and longitudinal compressibility. When the stent is elongated, it returns to an original relaxed state which is the final diameter of the stent. The stent is elongated and a sheath or a covering mechanism is loaded on top of the stent. This keeps the stent in a compressed state. The entire system is then introduced into a human body cardiovascular, vascular or non-vascular system and the sheath is slowly withdrawn either by pulling the sheath backwards or by moving the stent forwards. The stent slowly expands to its relaxed state and is implanted at a suitable site. If the stent is not implanted at the right area of the vascular system, it can be withdrawn again into the sheath, provided the complete stent has not been deployed yet. The sheath has also an inner core on which the coated stent is compressed and the sheath introduced on top of it. This inner core has four radiopaque markers on it which show the operator on an X-ray image the compressed length of the stent and also the relaxed length of the stent. Thus, the operator is able to clearly determine the length of the stent versus the diseased section of the vessel.

The above description has described specific structural details embodying the invention. However, it will be within one having skill in the art to make modifications without departing from the spirit and scope of the underlying inventive concept of this invention. The inventive concept is not limited to the structure and process described, but includes modifications and equivalents.

What is claimed is:

1. A method for making a stent comprising:
heat treating a plurality of wire strands;
coating the wire strands with a biocompatible fluoropolymer in an extruder to produce a plurality of coated wire strands;
spooling the coated wire strands; and
interlacing the coated wire strands from separate spools into a tightly held together monolayer integrated tubular shape, the tubular shape adapted to have axial and radial compressibility for insertion into a cardiovascular, vascular or non-vascular system of a human body.

2. The method as defined in claim 1 wherein the wire strands include a material selected from the group consisting of stainless steel, tungsten, titanium, nickel-titanium alloy, gold, silver or a combination thereof.

3. The method as defined in claim 1 wherein the fluoropolymer is selected from the group consisting of PTFE, ePTFE, FEP or a combination thereof.

4. The method as defined in claim 1 wherein at least one wire strand is employed in a coil pattern.

5. The method as defined in claim 1 wherein interlacing the coated wire strands is carried out in a knitting machine.

6. The method as defined in claim 5 wherein a brake mechanism on a spool supplying one coated wire strand causes the spool to supply such coated wire stand at a slower rate than other spools supplying the other coated wire strands.

7. The method as defined in claim 1 wherein textile strands are interlaced between the coated wire strands.

8. The method as defined in claim 7 wherein the textile strands include a material selected from the group consisting of polyester, polypropylene, polyethylene, polyurethane, polytetrafluoroethylene or a combination thereof.

9. The method as defined in claim 1 wherein at least one wire strand is preheated in an oven to impart an intended shape prior to coating.

10. The method as defined in claim 1 wherein the tightly held together monolayer integrated tubular shape allows for the exuding of blood for proper lumen wall function.

11. A method for making a stent comprising:
heating a plurality of wire strands to impart a desired shape to the wire strands;
coating each wire strand with a biocompatible polymer in an extruder to produce a plurality of coated wire strands; and
interlacing the coated wire strands to form a stent.

12. The method as defined in claim 11 further including regulating the speed of the wire strands in the extruder to provide a uniform coating.

13. The method as defined in claim 12 wherein interlacing includes braiding the coated wire strands in a braiding machine.

14. The method as defined in claim 13 further including spooling the coated wire strands onto spools, and wherein braiding includes removing the coated wire strands from the spools while braiding the coated wire strands in the braiding machine.

15. The method as defined in claim 14 further including regulating the speed of at least one of the spools at a slower rate than other spools.

16. The method as defined in claim 15 further including incorporating a fabric material between the braided, coated wire strands.

17. The method as defined in claim 16 further including preparing ends of the wire strands to prevent fraying.

18. The method as defined in claim 11 wherein interlacing includes knitting the coated wire strands in a knitting machine.

19. A method for making a stent comprising:
coating a plurality of wire strands with a biocompatible polymer and an adhesive in an extruder to produce a plurality of coated wire strands;
heating the coated wire strands to activate the adhesive; and
interlacing the coated wire strands to produce a stent.

20. A method for making a stent comprising:
interlacing a plurality of wire strands into a desired shape;
heating the wire strands in the desired shape;
removing the wire strands from the desired shape;
coating the wire strands with a biocompatible polymer; and
interlacing the wire strands to form a stent.

* * * * *